US012160005B2

(12) United States Patent
Deng et al.

(10) Patent No.: US 12,160,005 B2
(45) Date of Patent: Dec. 3, 2024

(54) BLACK METALLIC NANOROD ARRAYS AND METHOD OF MANUFACTURING THEREOF

(71) Applicant: Wayne State University, Detroit, MI (US)

(72) Inventors: Da Deng, Troy, MI (US); Minjun Bae, Detroit, MI (US)

(73) Assignee: Wayne State University, Detroit, MI (US)

( * ) Notice: Subject to any disclaimer, the term of this patent is extended or adjusted under 35 U.S.C. 154(b) by 87 days.

(21) Appl. No.: 17/396,031

(22) Filed: Aug. 6, 2021

(65) Prior Publication Data

US 2022/0045331 A1 Feb. 10, 2022

Related U.S. Application Data

(60) Provisional application No. 63/062,613, filed on Aug. 7, 2020.

(51) Int. Cl.
| | |
|---|---|
| *H01M 4/62* | (2006.01) |
| *H01M 4/02* | (2006.01) |
| *H01M 4/66* | (2006.01) |
| *H01M 4/70* | (2006.01) |
| *H01M 10/052* | (2010.01) |

(52) U.S. Cl.
CPC .......... *H01M 4/628* (2013.01); *H01M 4/661* (2013.01); *H01M 4/667* (2013.01); *H01M 4/70* (2013.01); *H01M 10/052* (2013.01); *H01M 2004/021* (2013.01); *H01M 2004/025* (2013.01)

(58) Field of Classification Search
CPC ...... H01M 6/628; H01M 4/661; H01M 4/667; H01M 4/70; H01M 10/052; H01M 2004/021; H01M 2004/025
See application file for complete search history.

(56) References Cited

U.S. PATENT DOCUMENTS

| | | | |
|---|---|---|---|
| 10,374,215 B2 | 8/2019 | Deng et al. | |
| 2009/0214942 A1* | 8/2009 | Frank | H01G 11/28 429/122 |
| 2010/0279003 A1 | 11/2010 | Au | |
| 2015/0233010 A1* | 8/2015 | Pan | H01M 4/0428 216/13 |
| 2015/0299889 A1 | 10/2015 | Mertens et al. | |
| 2018/0201513 A1* | 7/2018 | Kamali | C01B 33/023 |
| 2018/0223393 A1* | 8/2018 | Abayaweera | C22B 34/1204 |
| 2020/0091509 A1 | 3/2020 | Hryn et al. | |

FOREIGN PATENT DOCUMENTS

| | | |
|---|---|---|
| DE | 102012001912 A1 | 6/2013 |
| KR | 20160125806 A | 11/2016 |
| WO | 13/155276 A1 | 10/2013 |

OTHER PUBLICATIONS

International Search Report dated Dec. 23, 2021 for copending International App. No. PCT/US2021/045083.

* cited by examiner

*Primary Examiner* — Cynthia H Kelly
*Assistant Examiner* — Niara Trant
(74) *Attorney, Agent, or Firm* — Fishman Stewart PLLC (57) ABSTRACT

A device may include a metallic substrate and a plurality of nanorod arrays arranged on the substrate. The nanorod arrays may be made of porous metallic nanostructures and may appear black in color.

20 Claims, 9 Drawing Sheets

BLACK METALLIC NANOROD ARRAYS AND METHOD OF MANUFACTURING THEREOF

CROSS-REFERENCE TO RELATED APPLICATIONS

This application claims priority to U.S. Provisional Patent Application No. 63/062,613 filed on Aug. 7, 2020, the contents of which are hereby incorporated in its entirety.

GOVERNMENT LICENSE RIGHTS

This invention was made with government support under contract no. DE-EE0008236 awarded by the Department of Energy. The government has certain rights in the invention.

TECHNICAL FIELD

This disclosure relates generally to black metallic nanorod arrays that could be used in various applications, including, but not limited to, lithium-ion batteries.

BACKGROUND

Metals typically show metallic color with a smooth surface. Such metals are used in various applications, including, but not limited to, energy storage applications (lithium metal batteries, supercapacitors, etc.), biomedical applications, applications in defense/aerospace industries, and photochemical applications.

Advanced lithium-ion batteries (LIBs) are considered the powerhouses of the modern mobile society and find important applications in personal electronics, electric vehicles, and sustainable energy grids. The ever-increasing demand for high power, high energy and long cycle life cannot be fulfilled by existing conventional electrode materials. Taking a graphitic carbon anode for example, tis relatively low theoretical capacity of 372 mAh/g hinders further improvement. Therefore, carbon-alternative anode materials are highly sought after for next-generation LIBs. Lithium metal is considered one of the most promising alternative anode materials due to its low redox potential (−3.04V vs. SHE) and highest specific capacity (3860 mAh/g). Highly stable lithium metal anodes are also crucially important for the successful development of next-generation Li-ion batteries, as well as future lithium metal batteries including Lithium-Sulfur and Lithium-Air batteries. Unfortunately, Li metal anodes suffer well-documented issues of dendrite formation, poor stability, and poor safety.

A tremendous amount of efforts has been made to circumvent the issues of lithium dendrite formation. A few strategies have been introduced, such as electrolyte additives, solid-state electrolytes, artificial SEI coatings, and novel current collectors. Electrolyte additives, such as fluoroethylene carbonate, vinylene carbonate, and lithium polysulfides have been added in order to stabilize SEI. Unfortunately, low mechanical robustness of the SEI layer is still a hurdle to complete suppression of the Li dendrite formation for a long cycling. Additionally, there is a lack of sustainable electrolyte additives, as most of the known electrolyte additives are highly toxic chemicals. Recently, solid-state electrolytes have gained much attention due to its superior ability to physically suppress the Li dendrite formation. Nevertheless, limited ionic conductivity at room temperature, poor soli-solid contact, and increased interfacial impedance remain as challenges for meeting the desirable power requirements, especially under ambient conditions.

Another promising strategy to mitigate the dendritic Li growth is to build a conducive and lithiophilic 3D porous scaffold as it can effectively accommodate the infinite volume expansion of Li. More importantly, huge surface area provided by a highly porous structure can contribute to uniform Li electrodeposition by lowering the local current density, which can further postpone the initiation of Li dendritic growth according to the Sand's equation. Ideally, Li hosts should have high conductivity, electrochemical and structural stability. Ti is an attractive material for such application due to its high stability and conductivity. However, conventional planar Ti foil still induces the notorious Li dendrite formation.

Besides batteries, Ti metal also find many other applications. For example, in biomedical applications, Ti and its alloys have been extensively used as bone implants in bone repairing owing to the relatively low density, high mechanical and chemical stability and facile processing. However, bulk Ti and its alloy generally suffer from long-term implant loosening and relatively inferior biocompatibility to calcium phosphates.

In aerospace applications, Ti and its alloys have been extensively used due to the relatively low density and high mechanical strength. However, there may still be issues resulting from launch shock and corrosiveness.

Given such a wide range of applications of Ti, it is highly desirable to develop improved metals, such as a nanostructured Ti, to overcome the aforementioned challenges or shortcomings.

DETAILED DESCRIPTION

The present disclosure relates to devices incorporating black metallic and porous nanorod arrays that may be used in different applications. Generally, the device may include a metallic substrate with black metallic and porous nanorods arranged on the substrate.

Figure 1A:
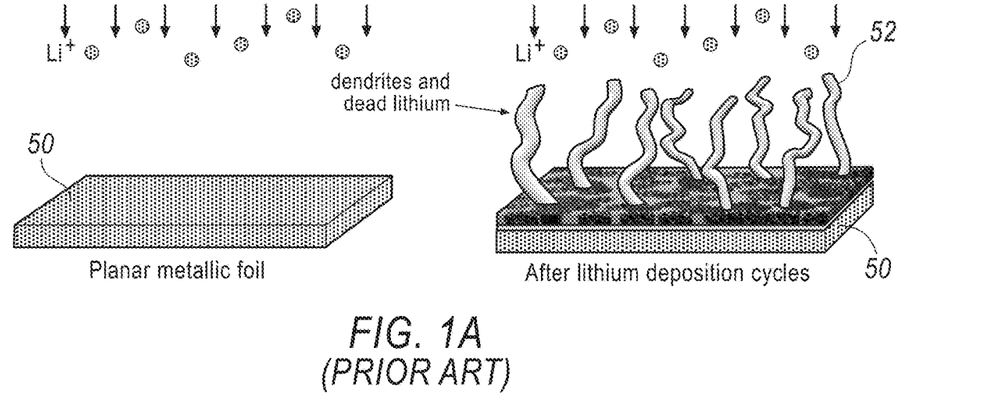
FIG. 1A is a schematic illustration of a traditional planar metallic foil before and after lithium deposition cycles with lithium dendrites and dead lithium formed.
Figure 1B:
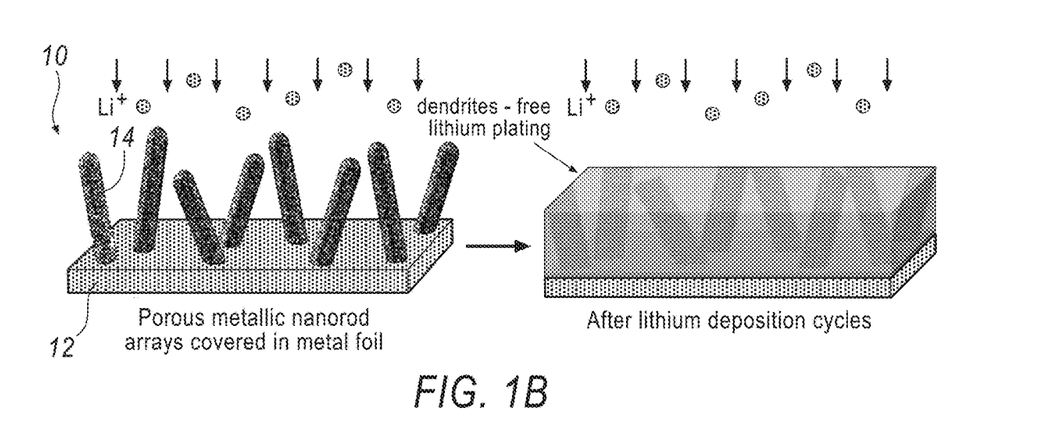
FIG. 1B is a schematic illustration of a porous metallic nanorod array before and after lithium deposition cycles according to teachings of the present disclosure forming dendrite-free electrodes.

Referring now to the figures, FIG. 1B illustrates one exemplary application in which the device is a lithium-ion or lithium-metal battery 10, where the substrate 12 is a foil acting as a current collector in order to achieve uniform lithium electrodeposition with long cycling life and without dendrites, as illustrated in FIG. 1B. For conventional planar metallic current collectors 50, the formation of lithium dendrites and dead lithium 52 upon lithium plating, as illustrated in FIG. 1A, share similarities to pure lithium metal anodes which suffer the issues of poor cyclability, low efficiency, dendrite formation and safety concerns. In contrast, by introducing a current collector 12 with porous and metallic nanorod arrays 14 covering the surface, the lithium plating characteristics could be positively manipulated. The large exposed surface in contact with electrolytes induced by the porous metallic nanorod arrays 14 and the highly conductive nature of the metallic nanorods could facilitate lithium deposition on the nanorods first, and lithium eventually fills the pores in the nanorods and pores between nanorods. The nanorod arrays could accommodate the uniform deposition of lithium. In other words, the presence of nanorod arrays could guide the deposition of lithium leading to no formation of lithium dendrites. Experimentally, superior functionality of the nanorod arrays was observed and dramatically improved lifespan of lithium metal anodes was achieved.

Figure 5:
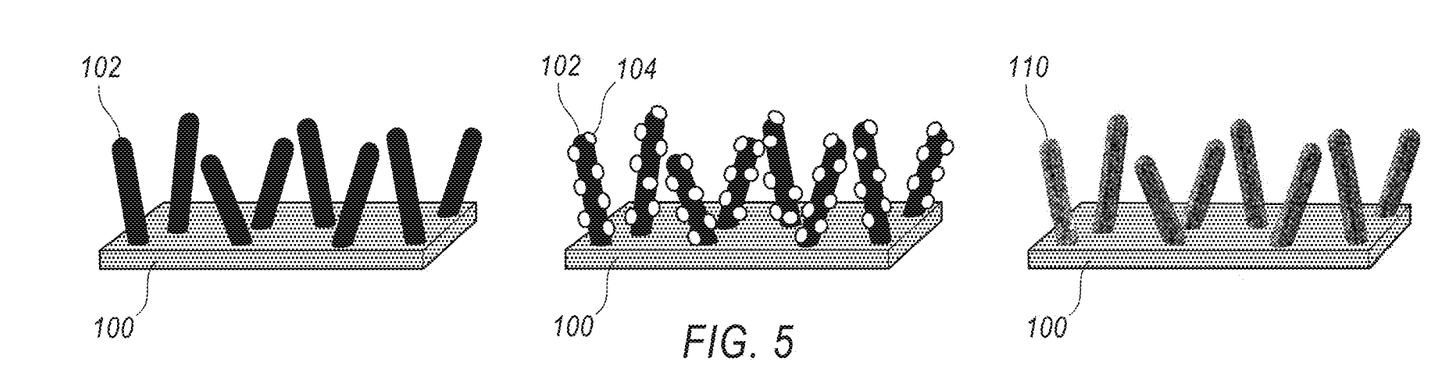
FIG. 5 shows the structure and composition changes involved for the precursor, intermediate and the product at different stages of synthesis.

While the metallic nanorod arrays are illustrated and described hereinafter with respect to Ti, it should be appreciated that other metals may be used, including, but not limited to, copper, iron, lead, nickel, tin vanadium, zinc, aluminum, silicon, and alloys thereof. Furthermore, the metallic nanorod arrays may have multi-directional reflection, nanoscale porosity, substructures, nanoarrays, surface coating, and/or large-scale manufacture An exemplary process for synthesizing porous metallic (e.g., Ti) nanorod arrays on a metal substrate (e.g., Ti foil) may first include hydrothermally treating a piece of the substrate 100 (e.g., 0.5×0.5 cm2), followed by acid treatment (e.g., HCl) and heating in an oven to get metal oxide (e.g., TiO$_2$) nanorod arrays 102 covering the metal substrate 100 as the starting material, as seen in the first (precursor) stage illustrated in FIG. 5. Then two pieces of the as-synthesized metal oxide nanorod arrays covered metal substrate may be put inside a crucible and Mg powder (e.g., 50 mg) may be spread around and near the supper stream in the crucible. The crucible may then be heated (e.g., at 650° C. for 4 h under the argon (100 sccm)), resulting in metallic nanorods 102 decorated by MgO nanoparticles 104 on the metal substrate 100, as seen in the second (intermediate) stage illustrated in FIG. 5. Subsequently, the foil 100 may be treated to remove extra Mg and MgO (e.g., with a copious amount of HCl solution (e.g., 0.5 M)) and then dried in a vacuum oven, resulting in the final porous, metallic nanorod arrays 110 on the metal substrate 100, as seen in the final phase illustrated in FIG. 5. The metallic nanorod arrays show a black color, in contrast to that of precursor metal oxide nanorod arrays, which may show typical metallic color. It is noteworthy that the resulting metallic nanorod arrays and the precursor metal oxide nanorod arrays do not exhibit much difference in morphologies except that the metallic nanorod arrays show high porosity. Given the melting point of Ti (1668° C.), the low temperature magnesiothermic reduction can effectively reduce TiO$_2$ to metallic Ti, but successfully preserve the nanorod arrays. After the reduction, the metallic nanorod arrays show a black color, in contrast to that of precursor metal oxide nanorod arrays, which may show a grey to white or metallic color. The dramatic color change is attributed to high porosity of metallic nanorod arrays obtained after the magnesiothermic reduction and further indicates successful transformation of TiO$_2$ to Ti.

It should be noted that the metallic Ti nanorod arrays were formed on the surface of Ti foil as the substrate, essentially formed a thin film, not in the form of powder. Based on SEM and TEM characterization, the surface area was about ~887.3 m$^2$ surface/m$^2$ substrate for the porous Ti nanorod arrays. Additionally, the black color indicates that light was absorbed and reflected due to the presence of the pores on the nanorods, decreasing the amplitude of forced vibration in narrow space. In other words, the nanorods are highly porous.

Figure 2A:
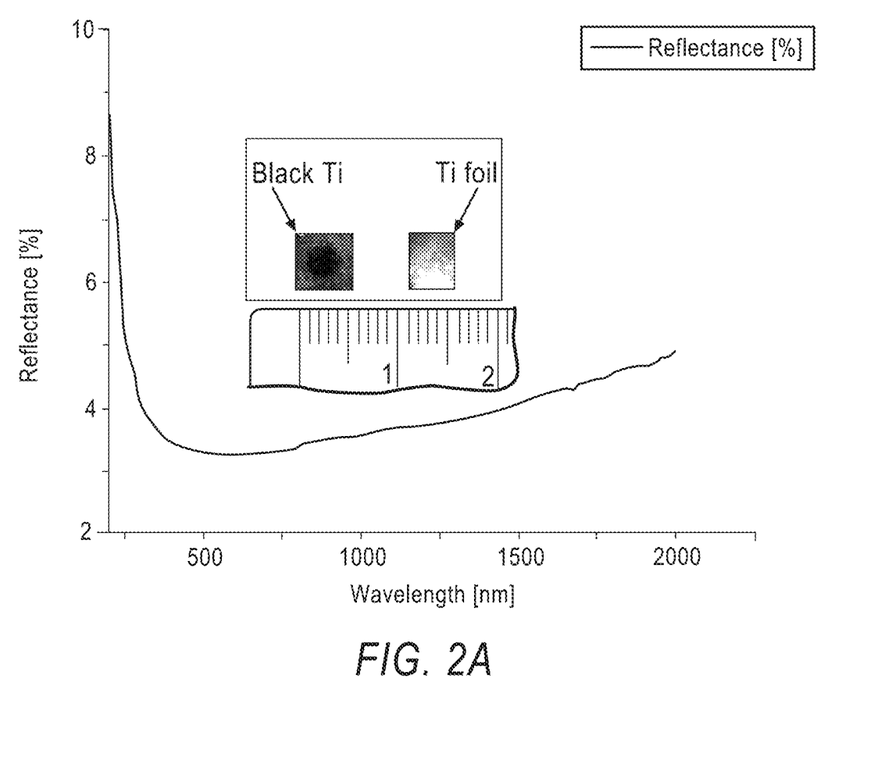
FIG. 2A is a spectral reflectance profile of black Ti nanorod arrays according to teachings of the present disclosure.
Figure 2B:
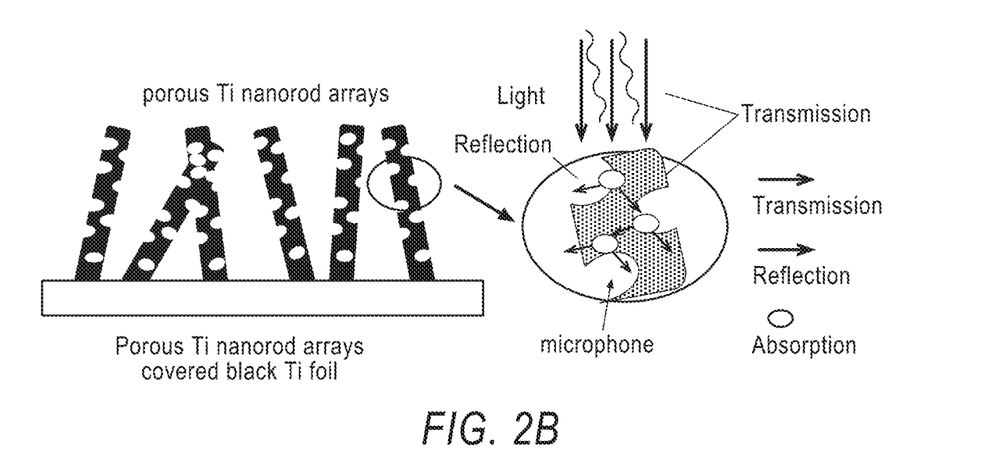
FIG. 2B is a schematic illustration of a process of black porous metallic Ti nanorod arrays on Ti foil absorbing incident light by decrease of the amplitude of forced vibration in narrow space according to teachings of the present disclosure.

The black color suggests the formation of porous metallic nanorods which can absorb nearly all the incident light by decrease of the amplitude of forced vibration in narrow space. In other words, the black color indirectly evidences the successful formation of porous metallic nanorod arrays on metal substrate. The black metal can reflect only less than 3.5% of most visible light and less than 4% of infra-red lights, as illustrated in FIG. 2A. The reflectance may be able to be further tuned and optimized by controlling the size of the micropores and microstructures and geometries of the nanorods. FIG. 2A shows optical images of a piece of the as-synthesized black metallic nanorod arrays on metal substrate (black color) as compared to a piece of original metal foil (silver color) on a background of black tap, and the spectral reflectance profile of the black metallic nanorod arrays. FIG. 2B is a schematic illustration of a plausible mechanism of black porous metallic nanorod arrays on the metal substrate absorbing nearly all the incident light by decrease of the amplitude of forced vibration in narrow space. The principle and process outlined here can be used to synthesized black colored metallic nanorod arrays of other metals beyond Ti.

Figure 3A:
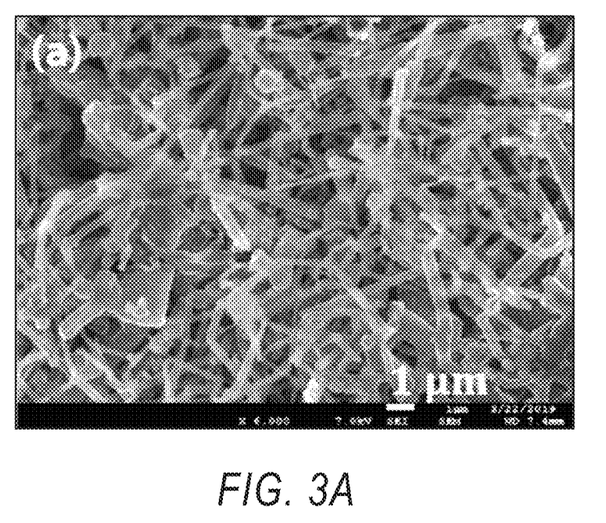
FIGS. 3A and 3B are FESEM (Field Emission Scanning Electron Microscope) images of a control sample of a planar Ti foil substrate and of metallic Ti nanorod arrays covered Ti foil after 24 mAh/cm² of Li electrodeposition, respectively, according to teachings of the present disclosure.
Figure 3B:
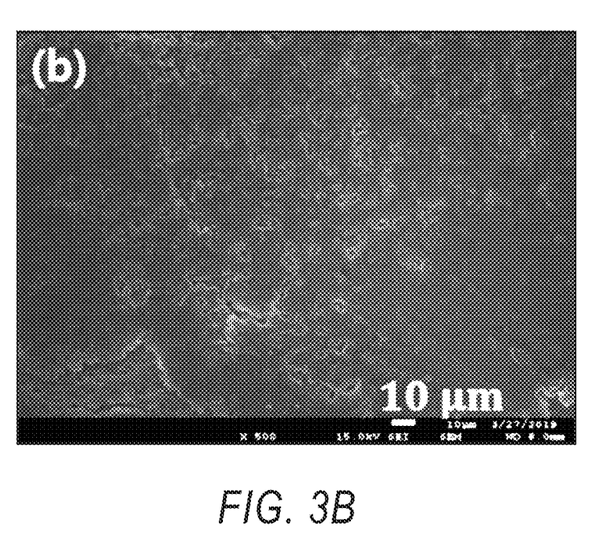

To demonstrate one of the potential applications of the metallic Ti nanorod arrays on Ti substrate, it was employed as current collectors for lithium metal anodes. The metallic Ti nanorod arrays covered Ti substrate have distinct advantages as a Li host: 1) numerous pores formed on the surface of nanorods provide numerous Li heterogeneous nucleation sites due to low energy barrier according to the conventional heterogeneous nucleation model, 2) meso and micro pores and robust Ti efficiently accommodate the infinite volume expansion of Li, 3) highly conductive 3D structured metallic Ti provides rapid electron pathway, 4) high Young's modulus of Ti can provide mechanical robustness and withstand high stress and 5) anti-corrosive and highly stable Ti can reduce the rate of electrolyte decomposition. The results suggest that a homogeneously distributed electric field was achieved by implementation of the metallic nanorod arrays as current collectors. The nanorod-based structures could accommodate intrinsic local volumetric fluctuation of lithium deposition and stabilize the SEI layer. The presence of porous metallic nanorod arrays provided preferential nucleation sites for lithium deposition and growth without the formation of dendrites. In the control experiments, when planar metallic substrate was used as a current collector, whisker-like dendrites were extensively formed on the surface after 24 hours of lithium plating; in contrast, dendrite-free surface was observed for metallic nanorod arrays covered metal substrate electrode under the same plating conditions. As seen in the FESEM images illustrated in FIGS. 3A and 3B, a control sample of planar metal substrate after 24 hours of lithium plating had whisker-like dendrites extensively formed on the surface (FIG. 3A), while in contrast, the metallic nanorod arrays covered metal substrate electrode had a dendrite-free surface under the same electrochemical conditions (FIG. 3B).

Figure 4A:
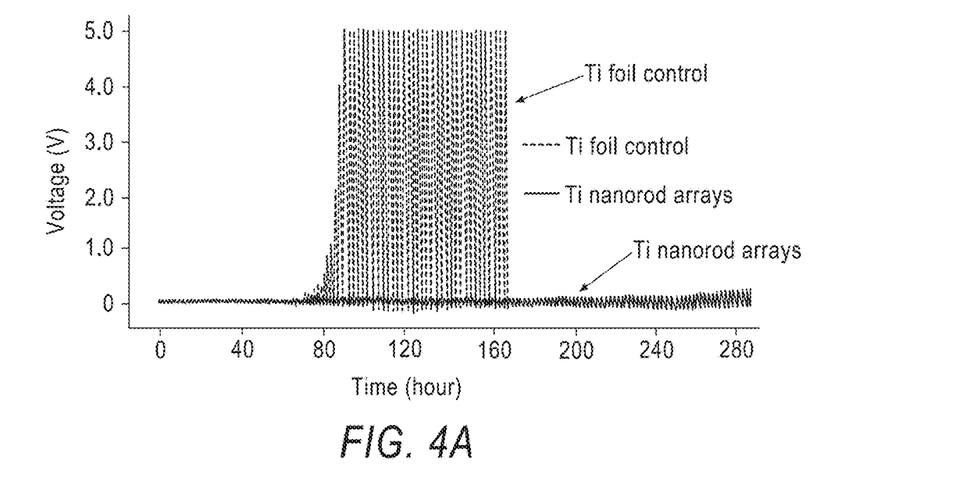
FIGS. 4A-4C are graphic illustrations of electrochemical characteristics of as-synthesized black Ti nanorod arrays for cycling stability, galvanostatic discharge/charge voltage profile between 19.5 and 24.5 hours, and between 68.5 to 73.5 hours, respectively, according to teachings of the present disclosure.
Figure 4B:
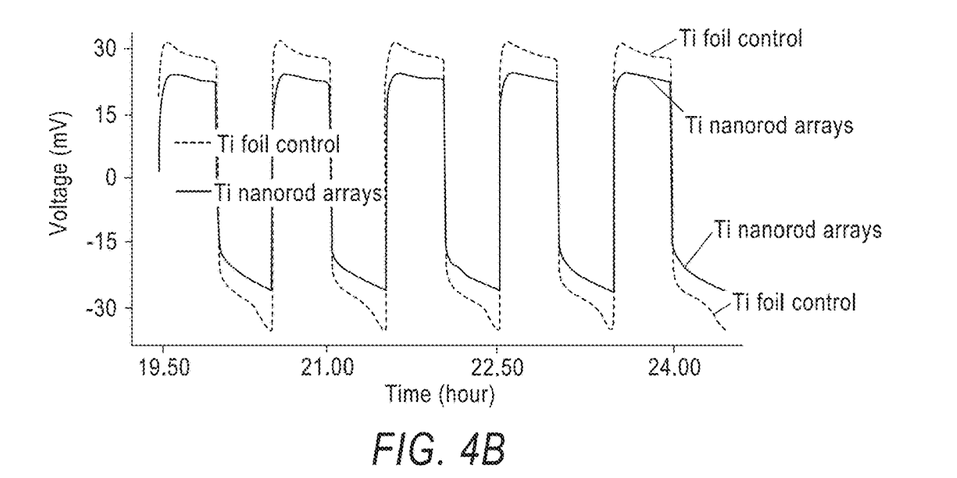
Figure 4C:
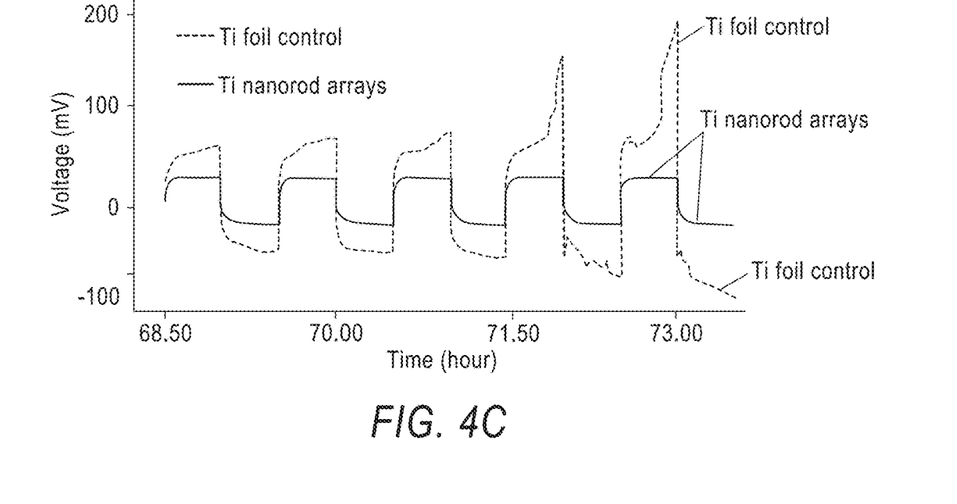

Referring now to FIGS. 4A-4C, FIG. 4 electrochemical characteristics of as-synthesized metallic Ti nanorod arrays as current collectors for lithium metal anodes, in comparison to that of control planar Ti metal substrate are illustrated. The electrochemical characteristics are: (a) cycling stability (FIG. 4A); (b) galvanostatic discharge/charge voltage profile between 19.5 and 24.5 hours (FIG. 4B), and (c) between 68.5 to 73.5 hours (FIG. 4C). Under the same testing conditions (e.g., Test current: 1 mA/cm2; test time: 1 hour/cycle; prelithation: 18 hours), metallic nanorod arrays demonstrated dramatically improved cycle stability as compared to that of planar metal substrate control. Voltage fluctuation was minimum in the first 100 cycles for metallic Ti nanorod arrays on Ti substrate. In contrast, extremely high voltage hysteresis and fluctuation was observed in 60 cycles for metal substrate control. (See FIG. 4A). For the planar Ti substrate, the observed voltage polarization implies increased interfacial resistance, capacity decay or short circuit caused by the lithium dendrites, dead lithium, and continuous SEI formation. In other words, metallic nanorod arrays on metal substrate can dramatically mitigate those issues associated with planar substrates. Efficiency of lithium stripping/plating significantly decreased in less than 100 cycles for the control metal substrate. On the other hand, almost no changes were observed for the metallic nanorod arrays over 300 cycles. Close examination of the stripping/plating profiles revealed that Ti nanorod electrode had a flat profile, while the planar Ti substrate gradually changed to huge overpotential fluctuation along with time, especially obvious after 68 cycles. For the planar Ti substrate control, dendrite formation and SEI accumulation is evidenced by overpotential fluctuation; in contrast, metallic nanorod arrays maintained flat cycling profiles and at lower over overpotential during cycling. This observation provided indirect evidence for the lithium dendrite formation as well as roughened electrode surface for planar metal substrate electrode, all of which lead to degraded effective current. In contrast, metallic nanorod arrays could overcome those issues with minimum overpotential fluctuation. In other words, the metallic nanorod arrays could facilitate the formation of stable SEI layer and enhance electrical connection without dendrite formation and less dead lithium during cycling. In contrast, the control metal substrate exhibited poor reversibility and low efficiency as expected. In a long-term galvanostatic cycling test, the metallic nanorod arrays can last for over 1400 hours indicating exceptional stability.

Figure 6A:
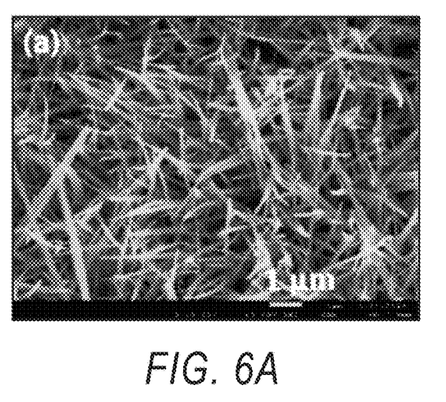
FIGS. 6A and 6B are top view FESEM images at different magnifications of TiO$_2$ nanorod arrays grown on Ti foil at a precursor stage according to teachings of the present disclosure.
Figure 6B:
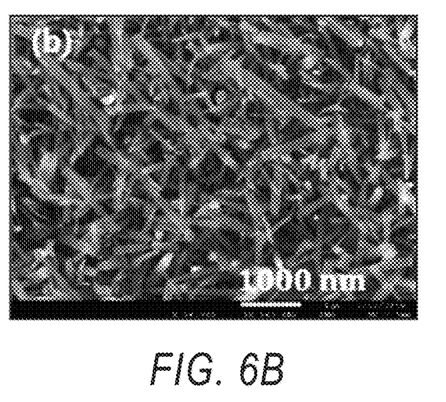
Figure 6C:
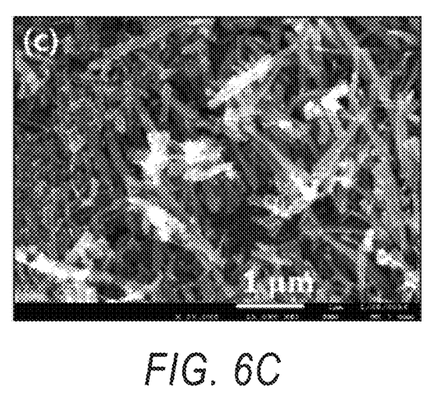
FIGS. 6C and 6D are top view FESEM images at different magnifications of Ti nanorod arrays on Ti foil with residues of Mg and MgO after magenesiothermic reactions at an intermediate stage according to teachings of the present disclosure.
Figure 6D:
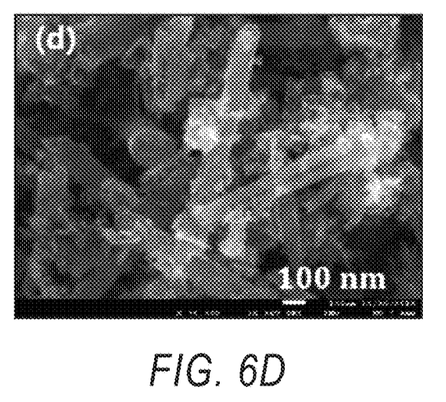
Figure 6E:
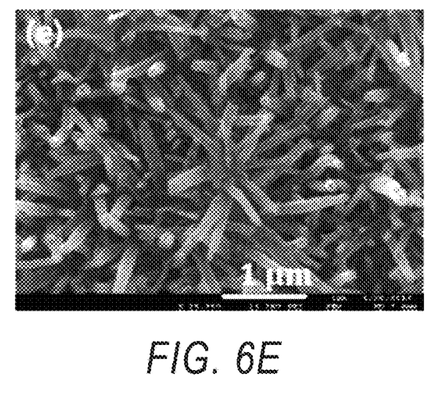
FIGS. 6E and 6F are top view FESEM images at different magnifications of porous metallic Ti nanorod arrays on Ti foil after etching off MgO as a final product according to teachings of the present disclosure.
Figure 6F:
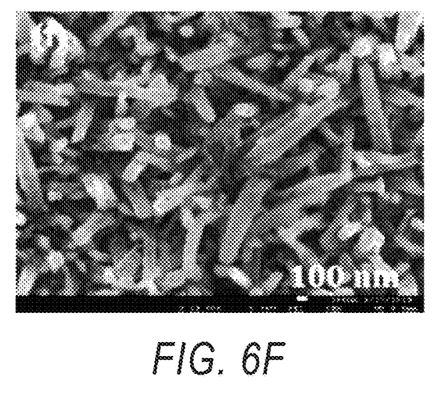

FIGS. 6A-F are top view FESEM images at different magnifications of the samples obtained at each stage of synthesis: (i) metal oxide (e.g., $TiO_2$) nanorod arrays grown on metal substrate (e.g., Ti foil) as precursor (FIGS. 6A and 6B); (ii) metallic (e.g., Ti) nanorod arrays on metal substrate (e.g., Ti foil) with residues of Mg and MgO after magenesiothermic reactions as intermediate (FIGS. 6C and 6D); and (iii) porous metallic (e.g., Ti) nanorod arrays on metal substrate (e.g., Ti foil) after etching off MgO by HCl as product (FIGS. 6E and 6F).

Figure 7A:
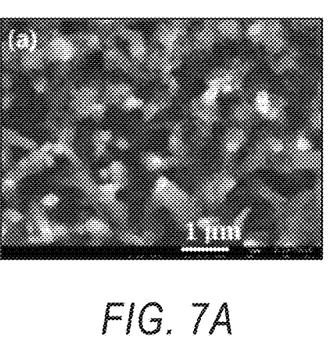
FIG. 7A is an FESEM image illustrating initial lithium electro-crystallization on external area of exposed porous Ti nanorod according to teachings of the present disclosure.
Figure 7B:
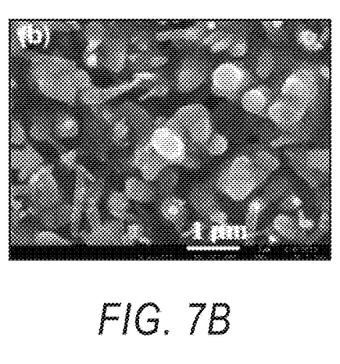
FIG. 7B is an FESEM image illustrating lateral growth on the surface of the nanorods or "fat nanorods" formed according to teachings of the present disclosure.
Figure 7C:
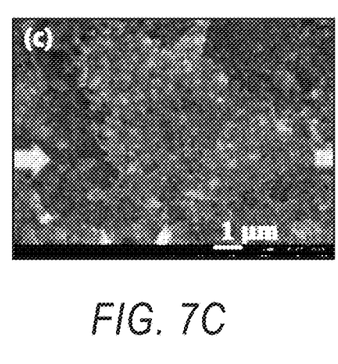
FIG. 7C is an FESEM image illustrating additional lithium filled up the pores between nanorods with light contrast dots indicating the tips of nanorods according to teachings of the present disclosure.
Figure 7D:
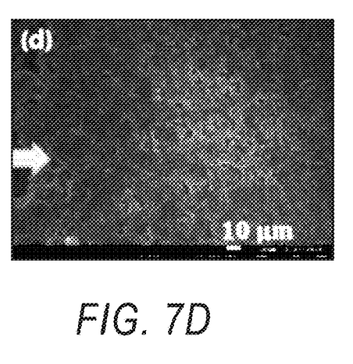
FIG. 7D is an FESEM image illustrating complete immersion of Ti nanorods with lithium with planar surface and no dendrites observed according to teachings of the present disclosure.

FIGS. 7A-7D are FESEM images showing the progress and changes of porous metallic (e.g., Ti) nanorod arrays on metal substrate (e.g., Ti foil) as a function of capacity of electrochemical lithium plating. FIG. 7A illustrates initial lithium electro-crystallization on external area of exposed porous metallic (e.g., Ti) nanorod. FIG. 7B illustrates lateral growth on the surface of the nanorods or "fat nanorods" formed. FIG. 7C illustrates additional lithium filled up the pores between nanorods with light contrast dots indicating the tips of nanorods. FIG. 7D illustrates complete immersion of metallic (e.g., Ti) nanorods with lithium with planar surface and no dendrites observed.

Figure 8:
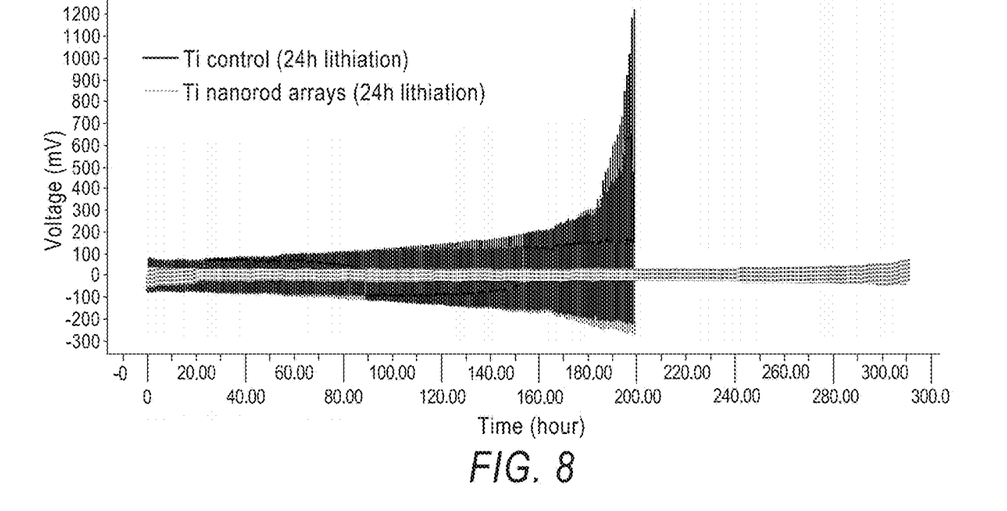
FIG. 8 is a graphic illustration of the cycling stability of the as-synthesized Ti nanorod arrays on a Ti foil as compared to control planar Ti foil as current collectors for lithium metal anodes according to teachings of the present disclosure.

FIG. 8 illustrates the cycling stability of the as-synthesized Ti nanorod arrays on a Ti foil as compared to control planar Ti foil as current collectors for lithium metal anodes. The testing conditions were the following: test current: 1 mA/cm$^2$; test time: 1 hour/cycle; lithation: 24 hours.

Figure 9:
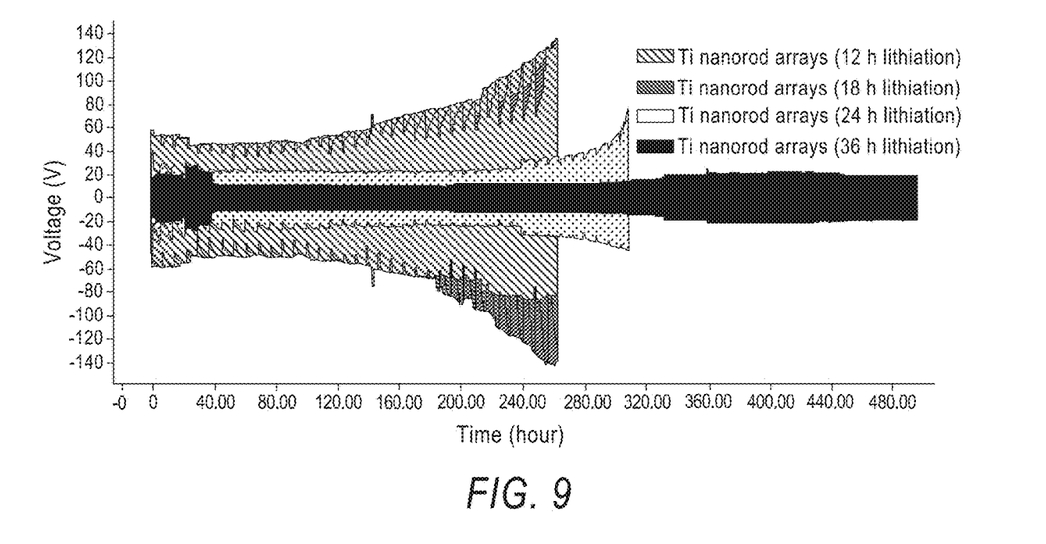
FIG. 9 is a graphic illustration of the cycling stability of the as-synthesized Ti nanorod arrays on a Ti foil lithiated with different capacities of lithium according to teachings of the present disclosure.

FIG. 9 illustrates cycling stability of the as-synthesized Ti nanorod arrays on a Ti foil lithiated with different capacities of lithium. The testing conditions were as follows: Test current: 1 mA/cm$^2$; test time: 1 hour/cycle; lithation: 12, 18, 24 and 36 hours. As seen from FIG. 9, the amount of Li lithiated on the Ti nanorod arrays could positively affect the cycling behaviors.

Recently, black metals have been attracting much attention. Black Au film was prepared by anodized aluminum oxide template-assisted approach. Small area of black gold was also prepared by femtosecond laser ablation. However, those two methods can only produce black gold on a very small scale and gold has poor strength-to-weight ratio. Ti is an important material for aerospace, biomedical, defense, energy, and chemical industries. Ti has good corrosion resistance and high strength-to-weight ratio. It is fairly stable, and has a density much smaller than that of stainless steel. It is interesting to develop unique Ti-based black materials that can be immediately integrated into existing aerospace, energy, biomedical and defense applications. The robust ultra-black metallic Ti can withstand launch shock and vibration. The black metallic Ti with tunable subwavelength microstructures should offer tremendous opportunities for making metal surface with excellent visible and infrared absorption. This black Ti may be used to make black devices for defense industries.

The excellent capability of our Ti nanorod arrays for incident light absorption in a wide range between 400 and 2000 nm is expected to be an excellent photocatalyst by harnessing a wide range of incident light to drive chemical transformations. As mentioned before, a passive oxygen layer can be formed on the surface of Ti nanorods under ambient conditions. It has been previously demonstrated that the adsorbed oxygen molecules can function as the electron acceptor without the presence of a semiconductor. According to the previous research, hot electrons can be transferred to the oxygen molecules to form $^3O_2$ molecules, and the subsequent oxidation reaction either through the vacant sites on the surface of the photocatalyst or the resulting $^3O_2$ molecules. Since $TiO_2$ is an extensively used material for photocatalysts, it is not hard to expect that our black Ti metal, which is highly stable due to the surface passivation layer, could drive photooxidation reactions with the light source.

Figure 10:
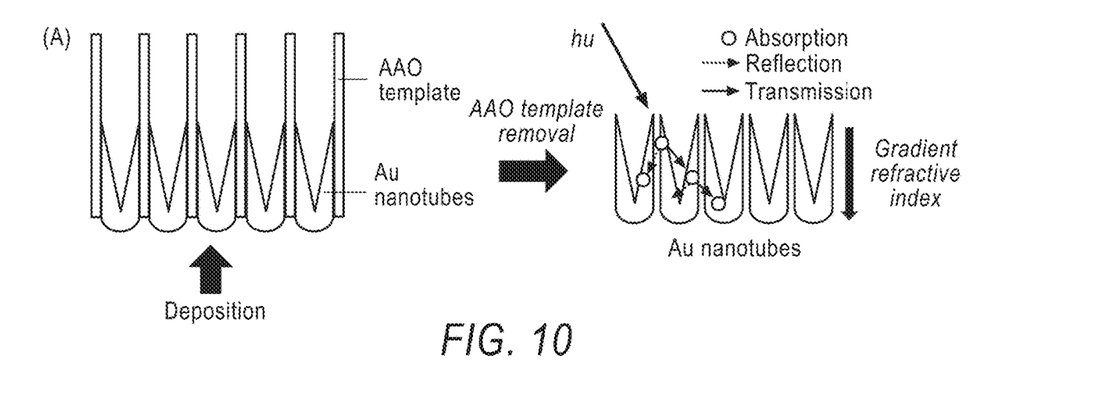
FIG. 10 is a graphic illustration of Au nanotube arrays according to teachings of the present disclosure.
Figure 11:
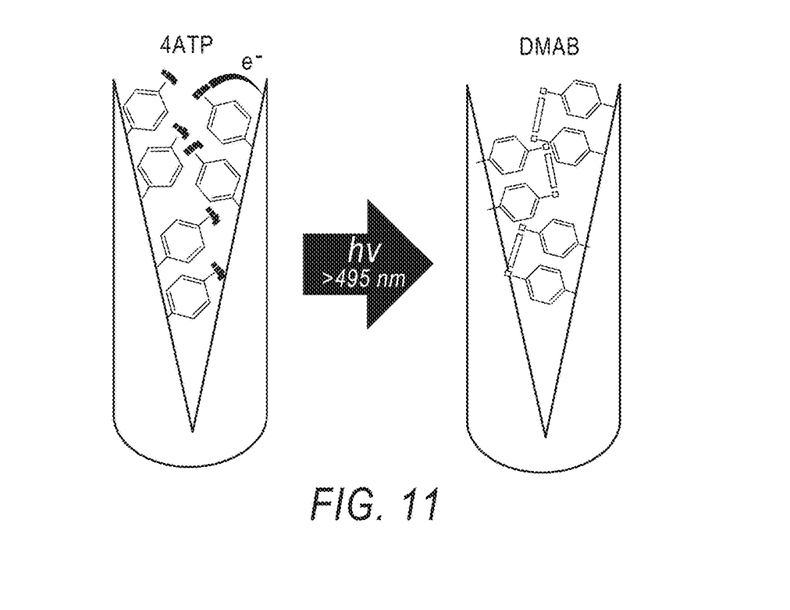
FIG. 11 is a graphic illustration of an oxidation process for the Au nanotube arrays of FIG. 10 according to teachings of the present disclosure.

Taking photochemical applications according to another exemplary embodiment, the metallic Ti nanorod arrays may perform similarly to the prior Au nanotubes. However, the Ti nanorod arrays are more cost effective than Au nanotubes and are different in structure. For fabrication of the black gold Au was sputtered on a porous AAO template followed by etching away AAO to obtain Au nanotubes arrays, as illustrated in FIG. 10. The as-prepared Au nanotube arrays was black in color, exhibiting high capabilities to absorb incident light. The black Au film was further utilized as a photocatalyst to drive the oxidation of 4-aminothiophenol (4ATP) to p,p-dimercaptoazobenzene (DMAB) under visible light irradiation. The oxidation process can be divided into three major steps: 1) direct attachment of 4ATP onto Au surface by simply soaking the Au film in a 4ATP solution, which is possible because of the thiol-gold interactions, 2) the formation of radical cations ($-NH_2^+$) derived from interactions between electrons injected from the electron-donating amino group ($-NH_2$) and holes formed onto Au surface, and 3) the formation of DMAB derived from the dimerization of the formed radical cations into a diphenylhydrazine and deprotonation, as illustrated in FIG. 11.

In another exemplary embodiment, the metallic black Ti nanorod arrays may be used as dental or orthopedic implant materials. Ti and its alloys have been extensively used as bone implants in bone repairing owing to the relatively low density, high mechanical and chemical stability and facile processing. Porous Ti nanorod arrays, due to its unique nanoscale porosity, can improve both biocompatibility and the integration with surrounding bone, resulting in enhanced cell adhesion and osteogenic differentiation. For example, Ti nanorod on commercial Ti foil fabricated via anodization exhibited improved protein absorbability and cell adhesions. Porous Ti can be also easily coated with biocompatible materials to further improve the biocompatibility. Our porous Ti nanorod arrays can be immediately applied in aforementioned applications. The Ti nanorod arrays have an average density of $(1.36 \pm 0.1) \times 10^{10}/cm^2$ (measured by counting the number of nanorods in $500 \times 500$ $nm^2$ of five random areas on SEM images). The porous nanostructures can effectively anchor functional materials, such as HAp and silver nanoparticles, to improve the biocompatibility and antimicrobial activity. Moreover, the mechanical properties of nanorod arrays, such as length, density and porosity are easily tunable by 1) the temperature and reaction time of the hydrothermal reaction and 2) the amount of Mg used in the magnesiothermic reduction. In other words, the mechanically tunable porous Ti nanorod arrays can be used as implantation materials with or without surface modification by functional materials. In addition, the excellent capability of our Ti nanorod arrays for near-infrared (NIR) light absorption is expected to have excellent photodynamic performance, which is very important feature for a photosensitizer to have in a light-triggered antibacterial and cancer therapy.

In another exemplary embodiment, the black Ti may be used to make black devices in defense or aerospace industries. Titanium and its alloys have been already extensively used for aerospace applications due to the relatively low density and high mechanical strength. Robust Ti can withstand the launch shock and is highly anti-corrosive. Combined with these inherent properties of Ti, owing to the unique multi-directional porous structure, our Ti nanorod arrays exhibit exceptional ability to trap incident light. It is black in color to naked eyes. The black Ti only reflects less than 3.5% and 4% of most visible light and infra-red light, respectively. Taking advantage of the exceptional ability to absorb light in such a wide wavelength, our black Ti might not be detected by an infrared sensor, which typically detects the infrared radiation reflected off of an object. In other words, a device made of our black Ti could only reflect less than 4% of incoming infrared light, giving off a significantly weak signal to the infrared sensors compared to traditional metals and alloys.

In yet another exemplary embodiment, the black Ti nanorod arrays have several features that are highly desirable in supercapacitors: 1) superior conductivity, 2) large surface area derived from the high porosity and multi-directional nature of nanorods and 3) thermal, mechanical and electrochemical stability. Owing to the abovementioned qualities, the black Ti can be used as a freestanding electrode for supercapacitors without the presence of binders and conductive agents, all of which often result in side reactions and non-uniform distribution of active materials. Taking advantage of biocompatibility of Ti, the black Ti might be used for implantable supercapacitor electrode as well. $TiO_2$ nanotube arrays have proved the potential for biocompatible/implantable supercapacitors. The metallic Ti nanorod arrays could deliver further improved performances in this applications, due to the aforementioned unique features/properties. In other words, our black Ti nanorod arrays may be used as an implantable biocompatible supercapacitors/batteries.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A device comprising:
a metallic substrate;
a plurality of nanorod arrays arranged on the substrate;
wherein the plurality of nanorod arrays are made from a process including:
forming metal oxide nanorod arrays on a metallic substrate;
spreading Mg on the metal oxide nanorod arrays;
heating the metal oxide nanorod arrays with Mg, resulting in metallic nanorod arrays;
removing excess Mg and MgO from the metallic nanorod arrays; and
drying the metallic nanorod arrays.

2. The device of claim 1, wherein at least one of the metallic substrate is foil and the metal is titanium.

3. The device of claim 1, wherein the metal is selected from a group comprising copper, iron, lead, nickel, tin, vanadium, zinc, aluminum, silicon, and alloys thereof.

4. The device of claim 1, wherein the device is a lithium-ion or lithium-metal battery, and the metallic substrate is a current collector.

5. A method for forming black metallic nanorod arrays, comprising:
forming metal oxide nanorod arrays on a metallic substrate;
spreading Mg on the metal oxide nanorod arrays;
heating the metal oxide nanorod arrays with Mg, resulting in metallic nanorod arrays;
removing excess Mg and MgO from the metallic nanorod arrays; and
drying the metallic nanorod arrays.

6. The method of claim 5, wherein the metal oxide is $TiO_2$.

7. The method of claim 5, wherein the metallic substrate is a metal foil.

8. The method of claim 5, wherein forming the metal oxide nanorod arrays includes:
hydrothermally treating a piece of the metal substrate;
treating the metal substrate with an acid; and
heating the metal substrate.

9. The method of claim 8, wherein the acid is HCl.

10. The method of claim 8, further comprising placing two pieces of the metal substrate with nanorod arrays in a crucible before spreading the Mg thereon.

11. The method of claim 10, wherein heating the metal oxide nanorod arrays with Mg is done in a crucible under argon.

12. The method of claim 5, wherein removing excess Mg and MgO is done by treating the metallic nanorod arrays with HCl.

13. The method of claim 5, wherein drying the metallic nanorod arrays is done in a vacuum oven.

14. A method for forming black metallic nanorod arrays, comprising:
forming metal oxide nanorod arrays on a metallic substrate;
spreading Mg on the metal oxide nanorod arrays;
heating the metal oxide nanorod arrays with Mg after said spreading Mg on the metal oxide nanorod arrays, resulting in metallic nanorod arrays;
removing excess Mg and MgO from the metallic nanorod arrays; and
drying the metallic nanorod arrays;
wherein the nanorod arrays are porous and appear black in color.

15. The method of claim 14, wherein the metal oxide is $TiO_2$ and the metallic substrate is a Ti foil.

16. The method of claim 14, wherein forming the metal oxide nanorod arrays includes:
hydrothermally treating a piece of the metal substrate;
treating the metal substrate with an acid; and
heating the metal substrate.

17. The method of claim 14, further comprising placing two pieces of the metal substrate with nanorod arrays in a crucible before spreading the Mg thereon.

18. The method of claim 17, wherein heating the metal oxide nanorod arrays with Mg is done in a crucible under argon.

19. The method of claim 14, wherein removing excess Mg and MgO is done by treating the metallic nanorod arrays with HCl.

20. The method of claim 5, wherein the metallic nanorod arrays have a black color once dried.

* * * * *